US012312604B2

United States Patent
Yliperttula et al.

(10) Patent No.: US 12,312,604 B2
(45) Date of Patent: *May 27, 2025

(54) CONTROLLING FREEZE-DRYING OF A HYDROGEL

(71) Applicant: UPM-KYMMENE CORPORATION, Helsinki (FI)

(72) Inventors: Marjo Yliperttula, Espoo (FI); Arto Merivaara, Helsinki (FI); Elle Koivunotko, Helsinki (FI); Kalle Manninen, Helsinki (FI); Sami Valkonen, Kuopio (FI); Markus Nuopponen, Helsinki (FI); Lauri Paasonen, Järvenpää (FI)

(73) Assignee: UPM-KYMMENE CORPORATION, Helsinki (FI)

( * ) Notice: Subject to any disclaimer, the term of this patent is extended or adjusted under 35 U.S.C. 154(b) by 89 days.

This patent is subject to a terminal disclaimer.

(21) Appl. No.: 17/245,368

(22) Filed: Apr. 30, 2021

(65) Prior Publication Data

US 2022/0348882 A1 Nov. 3, 2022

(51) Int. Cl.
  *C12N 5/09* (2010.01)
  *C12N 5/00* (2006.01)
  *B82Y 5/00* (2011.01)
  *B82Y 30/00* (2011.01)
  *B82Y 40/00* (2011.01)

(52) U.S. Cl.
  CPC ......... *C12N 5/0693* (2013.01); *C12N 5/0062* (2013.01); *C12N 5/0075* (2013.01); *B82Y 5/00* (2013.01); *B82Y 30/00* (2013.01); *B82Y 40/00* (2013.01); *C12N 2513/00* (2013.01); *C12N 2533/78* (2013.01)

(58) Field of Classification Search
  CPC .. C12N 5/0693; C12N 5/0062; C12N 5/0075; C12N 2513/00; C12N 2533/78; C12N 2500/34; B82Y 5/00; B82Y 30/00; B82Y 40/00; A61K 47/38
  See application file for complete search history.

(56) References Cited

FOREIGN PATENT DOCUMENTS

| CN | 107722338 A | 2/2018 | |
|---|---|---|---|
| EP | 2 779 996 A | 9/2014 | |
| EP | 2857583 A1 | 4/2015 | |
| EP | 2 794 846 B1 | 8/2017 | |
| EP | 3 335 695 A1 | 6/2018 | |
| EP | 2 900 806 B1 | 11/2020 | |
| WO | WO 2013/072563 A1 | 5/2013 | |
| WO | WO 2018/109281 A1 | 6/2018 | |
| WO | WO-2018108341 A1 * | 6/2018 | ........... A01N 1/0221 |

OTHER PUBLICATIONS

Nahr et al., LWT-Food Science and Technology 64 (2015) 326-332 Optimization of the nanocellulose based cryoprotective medium to enhance the viability of freeze dried Lactobacillus plantarum using response surface methodology (Year: 2015).*
Autissier et al. Fabrication of porous polysaccharide-based scaffolds using a combined freeze-drying/cross-linking process; Acta Biomaterialia 6 (2010) 3640-3648 (Year: 2010).*
Dufresne et al., Freeze-dried plasma proteins are stable at room temperature for at least 1 year Clin Proteom (2017) 14:35 (Year: 2017).*
Cassanelli, M., Norton, I. and Mills, T., 2018. Interaction of mannitol and sucrose with gellan gum in freeze-dried gel systems. Food biophysics, 13, pp. 304-315. (Year: 2018).*
Extended European Search Report in European Patent Application No. EP 21171457.1, mailed Oct. 18, 2021 (7 pages).
Paukkonen H. et al. "Nanofibrillar cellulose hydrogels and reconstructed hydrogels as matrices for controlled drug release" (pp. 12).
Bhattacharya et al., "Nanofibrillar cellulose hydrogel promotes three-dimensional liver cell culture", Journal of controlled release: official journal of the Controlled Release Society. 164 (2012) 291-8 (pp. 8).

* cited by examiner

*Primary Examiner* — Jeremy C Flinders
*Assistant Examiner* — Masudur Rahman
(74) *Attorney, Agent, or Firm* — NIXON PEABODY LLP

(57) ABSTRACT

The present disclosure relates to a method for controlling freeze-drying of a hydrogel wherein the method comprises adjusting the residual water content of the freeze-dried hydrogel, and to a freeze-dried hydrogel composition comprising nanoscale cellulose and a at least one biomolecule selected from an oligosaccharide or a disaccharide. The present disclosure further concerns the use of the freeze-dried hydrogel composition for cell culturing, a cell culturing scaffold as well as a process for manufacturing a reconstituted hydrogel.

6 Claims, 8 Drawing Sheets

CONTROLLING FREEZE-DRYING OF A HYDROGEL

FIELD OF THE DISCLOSURE

The present disclosure relates to a method for controlling freeze-drying of a hydrogel comprising nanoscale cellulose wherein the method comprises adjusting the residual water content of the freeze-dried hydrogel, and to a freeze-dried hydrogel composition comprising nanoscale cellulose, at least one biomolecule selected from an oligosaccharide and a disaccharide, and a preferred residual water content. The present disclosure further concerns the use of the freeze-dried hydrogel composition for cell culturing, a cell culturing scaffold as well as a process for manufacturing reconstituted hydrogel.

BACKGROUND OF THE DISCLOSURE

In recent years, cellulose based hydrogel nanomaterials with biodegradable and biocompatible features, have emerged the interest in different biopharmaceutical applications. Cellulose based hydrogel nanomaterials are of particular interest based on their inherent properties and similarities with physiological matrices.

In order to enable more feasible transportation possibilities of the material and improve the storage properties at room temperature, drying of for example wood-based native nanofibrillar cellulose (NFC) hydrogel has been researched.

Freeze-drying, which is a widely used desiccation method to improve shelf life and handling of the heat sensitive products is one method for preservation of heat-sensitive substances. However, hydrophilicity of the fibrils of the nanocellulose as well as their tendency to aggregate during a drying process, have created obstacles in drying trials of NFC hydrogel. Moreover, freeze-drying sometimes damages the product and further there can be changes in the properties of the product during long-term storing.

Despite the ongoing research and development in preserving cellulose based hydrogel nanomaterials, there is still a need to provide an improved method for preservation of hydrogels comprising nanoscale cellulose.

BRIEF DESCRIPTION OF THE DISCLOSURE

An object of the present disclosure is to provide a method for controlling freeze-drying and reconstitution of a hydrogel comprising nanoscale cellulose, by adjusting the residual water content of the freeze-dried hydrogel. In some embodiments of the disclosure, the method comprises adding a biomolecule to the hydrogel before freeze-drying the hydrogel and/or optimizing the freeze-drying cycle for example by taking into account the Tg' (glass transition temperature of maximally freeze-concentrated sample) of the mixture comprising hydrogel and a biomolecule. Typically, the hydrogel comprises nanoscale cellulose, such as nanofibrillar cellulose and at least one biomolecule selected from an oligosaccharide or a disaccharide.

The disclosure is based on the idea of a desire to identify how to control and steer freeze-drying of a hydrogel for example ensuring successful reconstitution of the freeze-dried hydrogel and understanding the molecular level interactions with water during freeze-drying.

An advantage of the method and of the freeze-dried hydrogel composition of the disclosure is that the freeze-dried hydrogel can be stored at room temperature (20-25° C.) for a long time, even over a year and reconstituted maintaining the properties of the hydrogel used for freeze-drying. The freeze-dried hydrogel may be reconstituted to a preferred shape, concentration and/or consistency.

A further advantage of freeze-dried hydrogel composition of the disclosure is that it can be used for cell culturing and in a process for manufacturing a cell culturing scaffold. Since the optimized hydrogel concentrations for cell culturing differ for different cells, it is advantageous that hydrogel of different concentrations can be used for freeze-drying and that the freeze-dried hydrogel can be reconstituted to the original concentration or to a different concentration.

A further advantage is that by the method of the disclosure the temperature of the primary drying can be increased considerably. This has a major impact from a time consumption and financial point of view, since already a 1° C. increase in the sample during freeze-drying could decrease the time required for the primary drying remarkably.

The process of the disclosure is especially suitable when hydrogel comprising nanoscale cellulose, such as native nanofibrillar cellulose are freeze-dried for example for use in cell culturing.

BRIEF DESCRIPTION OF THE DRAWINGS

In the following the disclosure will be described in greater detail by means of preferred embodiments with reference to the accompanying drawings, in which.

DETAILED DESCRIPTION OF THE DISCLOSURE

Figure 1A:
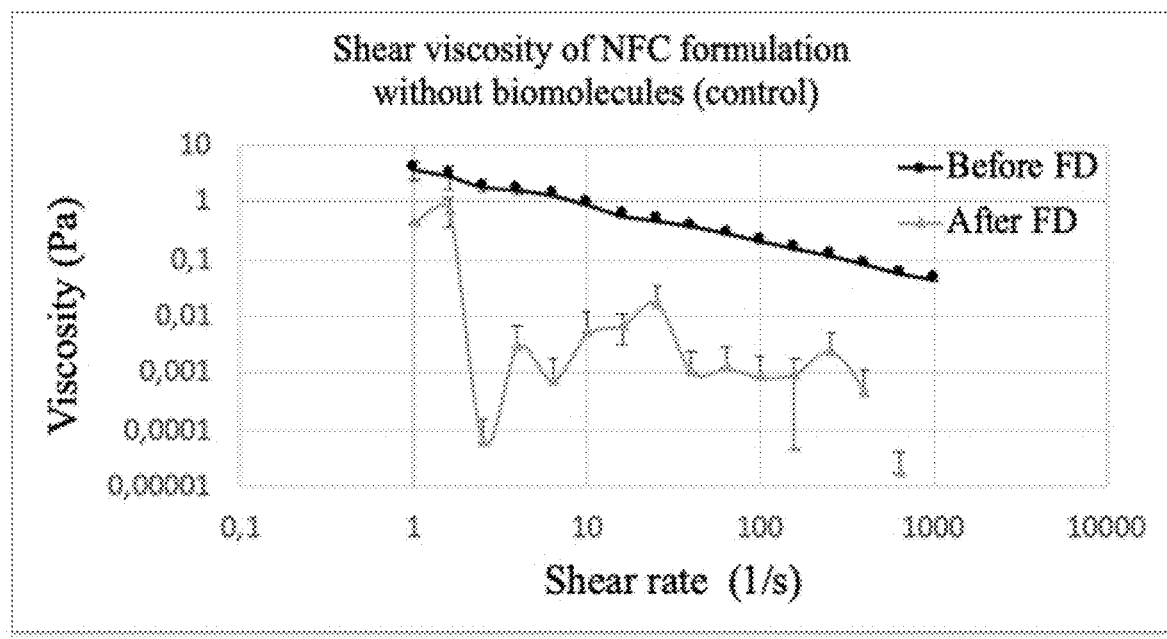
FIG. 1A shows shear rate viscosity before freeze-drying (FD) and after the reconstitution of the freeze-dried cake from nanofibrillar cellulose (NFC) hydrogel composition without biomolecules (mean±S.D., n=3)

In order to enable storage at room temperature and successful reconstitution of freeze-dried hydrogel, which are particularly suitable in cell culturing scaffolds, a method for controlling freeze-drying of a hydrogel, comprising nanoscale cellulose, is provided.

It has surprisingly been found that by adjusting the residual water content of the freeze-dried hydrogel composition it was possible to control the freeze-drying and/or reconstitution of a hydrogel comprising nanoscale cellulose. For example, by using a biomolecule as cryoprotectant or lyoprotectant when freeze-drying hydrogel comprising nanoscale cellulose, such as nanofibrillar cellulose, it was found, that it was possible to adjust the residual water content of the freeze-dried hydrogel composition, thus improving and controlling the reconstitution of the freeze-dried hydrogel composition. Typically, the biomolecule is one or more of an oligosaccharide, such a trisaccharide or a disaccharide and the adjusting is done by optimizing the amount of biomolecule added to the composition.

According to some embodiments of the disclosure, the method comprises adding a biomolecule to the hydrogel comprising nanoscale cellulose before freeze-drying the hydrogel. Typically, the biomolecule is selected from an oligosaccharide or a disaccharide, preferably a disaccharide or a mixture of several disaccharides, more preferably a disaccharide, most preferably lactose (4-O-β-D-galactopyranosyl-D-glucopyranose), trehalose (α-D-glucopyranosyl-α-D-glucopyranoside) or sucrose (β-D-fructofuranosyl-α-D-glucopyranoside). Trehalose and sucrose typically both have high glass transition temperatures and hydrogen bonding abilities. An amino acid, such as glycine may be added for example to improve the attraction of a poly- or disaccharide to the cellulose. Typically the amino acids are; charged amino acids such as arginine, lysine, aspartic acid or glutamic acid; polar amino acids such as glutamine, asparagine, serine, threonine, tyrosine, histidine or cysteine; amphipatic amino acids, such as tryptophan, tyrosine or methionine; or hydrophobic amino acids, such as glycine, alanine, valine, isoleucine, leucine, proline, phenylalanine or methionine preferably one of glycine, tryptophan, leucine and/or glutamine.

According to some embodiments of the disclosure, the freeze-drying of the hydrogel of the disclosure can be controlled by utilizing a freeze-drying cycle taking into account the Tg' (glass transition temperature of maximally freeze-concentrated sample) of the mixture comprising the hydrogel and the biomolecule by ensuring that the temperature does not exceed the glass transition temperature of maximally freeze-concentrated sample (Tg).

In the present specification and claims, the following terms have the meanings defined below.

The term nanoscale cellulose refers to nanofibrillar cellulose and/or nanocrystals. As used herein, the term nanofibrillar cellulose, nanofibrils or nanofibrillated cellulose or NFC is understood to encompass plant-derived nanofibrillar structures including fibrils and fibril bundles liberated from cellulose-based fiber material, or cellulose pulp. The nanofibrillar structures liberated from cellulose-based fiber raw material are characterized by a high aspect ratio (length/diameter): their length may exceed 1 µm, whereas the diameter typically remains smaller than 200 nm. The smallest nanofibrils are in the scale of elementary fibrils, the diameter being typically in the range of 2-12 nm. The dimensions and size distribution of the fibrils depend on the disintegration method and efficiency, and on pretreatment. Typically the median length of fibrils or fibril bundles in NFC is not greater than 100 µm, for example in the range of 1-50 µm, and the number average diameter of the fibrils or fibril bundles is smaller than 200 nm, suitably in the range of 2-100 nm. Intact, unfibrillated microfibril units may be present in the nanofibrillar cellulose but only in insignificant amounts. The nomenclature relating to nanofibrillar celluloses is not uniform and there is an inconsistent use of terms in the literature. For example, the following terms have been used as synonyms for nanofibrillar cellulose: cellulose nanofiber, nanofibril cellulose (CNF), nanofibrillar cellulose, nano-scale fibrillated cellulose, microfibrillar cellulose, cellulose microfibrils, microfibrillated cellulose (MFC), and fibril cellulose. As used herein, the nanofibrillar cellulose is not meant to encompass non-fibrillar, rod-shaped cellulose nanocrystals or whiskers. Nanocrystals are a highly crystalline material called cellulose nanocrystals (CNC), nanocrystals of cellulose (NCC) or cellulose nanowhiskers (CNW). The nanocrystals are rod-like and stiff, have a narrow size distribution and are shorter than nanofibrils. The nanocrystals also have lower viscosity and yield strength and are not as good at holding water as nanofibrillar cellulose.

The term biomolecule, also called biological molecule, is a substance that is produced by cells and living organisms. Biomolecules have a wide range of sizes and structures as well as variety of functions. The four major types of biomolecules are carbohydrates, lipids, nucleic acids, and proteins. As used herein, especially relevant biomolecules are carbohydrates, preferably oligosaccharides, such as trisaccharide as well as disaccharides. The disaccharides can be reducing saccharides, such as lactose, maltose and cellobiose or non-reducing disaccharides, such as trehalose and sucrose, preferably the disaccharides are non-reducing disaccharides.

Also, amino acids may be used as biomolecules together with the oligosaccharide and/or disaccharide. The amino acids may be; charged amino acids such as arginine, lysine, aspartic acid or glutamic acid; polar amino acids such as glutamine, asparagine, serine, threonine, tyrosine, histidine or cysteine; amphipatic amino acids, such as tryptophan, tyrosine or methionine; or hydrophobic amino acids, such as glycine, alanine, valine, isoleucine, leucine, proline, phenylalanine or methionine.

Typically, a freeze-drying process is divided into three main steps: 1) Freezing (solidification of a sample), 2) primary drying (sublimation of frozen water) and 3) secondary drying (removal of unfrozen water).

The term freezing step, refers to the first step of freeze-drying where the temperature of a composition is lowered below its freezing point to solidify the sample. The freezing of water solution, or crystallization in general, consists of two steps: 1) nucleation and 2) the growth of nuclei to the macroscopic crystals. The driving force of nucleation is mainly defined by supercooling. As the temperature drops below the freezing point of the solution, the probability to form thermodynamically favourable ice clusters, which act as nuclei for ice crystallization, grows.

The term primary drying refers to the main step of drying and is usually the longest phase in the freeze-drying process. During the primary drying step, the frozen solid water (ice) is sublimated under vacuum. The driving force of sublimation is the vapor pressure difference (the temperature difference) between the frozen water and the surface of the condenser.

The term secondary drying refers to the last part of freeze-drying were any unfrozen water still present in the sample is removed. Secondary drying can be performed at elevated temperatures because the ice has been removed during the primary drying and thus the risk of melting or collapsing is minimal. Especially for amorphous materials, temperature elevation is preferably performed with slow ramp (about 1° C./min) to avoid collapsing.

Dryness, i.e. moisture content (or residual moisture content) of a freeze-dried product is typically determined by gravimetric analysis. The amount of water is determined by subtracting the dry weight from the initial weight. The moisture content is then calculated as the amount of water divided by the dry weight or total weight, depending on the reporting method. Another method of describing dryness is the dry substance content (DS content), also called dry matter content. DS is the percentage of solids in a mixture of substances and the unit of DS content is % by weight. The higher this proportion, the drier the mixture.

The term residual water refers to the water of the freeze-dried composition, which is not released during the secondary drying, i.e. the residue water remaining in/on the freeze-dried hydrogel composition comprising nanoscale cellulose, such as nanofibrillar cellulose. The residual water content of a freeze-dried hydrogel composition comprising nanoscale cellulose, such as nanofibrillar cellulose can be measured by Karl Fischer titration. Water, which is not released from the composition during the primary drying, but which is removed during the secondary drying is called bound water.

The term glass transition temperature of maximally freeze concentrated sample (Tg') refers the temperature where the composition has gone through glass transition. i.e. the freeze-concentration of solutes has increased the viscosity of the solution until no more solid ice can form.

The term reconstitution refers to the process of restoring something dried to its original state by adding reconstitution media, for example water and/or cell medium to it. The reconstitution can be into original state or e.g. into a different concentration or stiffness by adding less reconstitution media than the released water.

According to the embodiments of the disclosure nanoscale cellulose is chosen from nanofibrillar cellulose and/or nanocrystals, preferably from native nanofibrillar cellulose and/or nanocrystals, more preferably the nanoscale cellulose is nanofibrillar cellulose, most preferably native nanofibrillar cellulose. In a hydrogel comprising nanofibrillar cellulose, the total fiber content is typically 0.5% to 5%, preferably 0.7% to 3%, more preferably 0.8% to 2.5%, most preferably about 0.8% or 2% (m/v).

Typically, in the embodiments of the disclosure, the freeze-drying of the method comprises a freezing step, a primary drying and a secondary drying. According to some embodiments of the disclosure the freeze-drying comprises a freezing step, preferably performed at a temperature between −40° C. and −60° C. for 1-5 hours, at a pressure ATM, after gradually decreasing the temperature 0.5-2° C./min, preferably about 1° C./min, a primary drying during which temperature is increased 0.5-2° C./min, preferably about 1° C./min till a temperature between −40° C. and −50° C. and the pressure is decreased to a pressure between 30 mTorr to 100 mTorr, preferably about 50 mTorr and thereafter keeping the temperature for 2-120 hours, preferably 10 to 100 hours, more preferably 50 to 100 hours and/or a secondary drying where the temperature is gradually increased 0.5-2° C./min, preferably about 1° C./min from a temperature between −40° C. and −50° C. to room temperature (+20° C.-25° C.) and keeping the temperature for 0.5 to 5 hours, preferably 1 to 2 hours. The primary drying can be determined with a comparative pressure measurement using a capacitance manometer (absolute pressure, CM) and pirani gauche (relative vacuum).

Typically, in the embodiments of the disclosure, hydrogel compositions are prepared by mixing different concentrations of biomolecules with water, such as ultrapure water, for example MQ-water, which are then combined with a hydrogel comprising nanoscale cellulose, such as nanofibrillar cellulose, to the wanted total fiber content (m/v). Alternatively, biomolecule(s) are added as a part of the nanofibrillar cellulose production process before freeze-drying. Preferably the hydrogel compositions are homogenized by mixing them with conventional techniques, for example with vortex or for compositions of higher concentration with syringe technique. The total concentration of the biomolecules in the hydrogel compositions is typically selected from an amount between 100 mM to 700 mM, preferably 150 mM to 500 mM and more preferably 150 mM to 300 mM of the total concentration of the mixture, including the amount being chosen from a range between two of the following 100 mM, 125 mM, 150 mM, 175 mM, 200 mM, 225 mM, 250 mM, 275 mM, 300 mM, 325 mM, 350 mM, 375 mM, 400 mM, 425 mM, 450 mM, 475 mM, 500 mM, 550 mM, 600 mM, 650 mM and 700 mM.

The method of the disclosure typically comprises the following steps
a) providing a hydrogel comprising nanoscale cellulose;
b) providing at least one biomolecule selected from an oligosaccharide, a disaccharide or a combination of any of them;
c) mixing the hydrogel of step a) with the biomolecule of step b) to obtain a mixture; and
d) freeze-drying the mixture of step c) to obtain a freeze-dried hydrogel comprising nanoscale cellulose.

By utilizing the method of the disclosure, freeze-drying of hydrogel is controlled. The freeze-dried hydrogel composition typically comprises a hydrogel comprising nanoscale cellulose and biomolecule. It has been shown that the residual water content of the freeze-dried hydrogel composition can be adjusted in order to control reconstitution of the freeze-dried hydrogel. Without committing ourselves to any explanatory model, a preliminary observation suggests that in addition to binding water to themselves, adding a biomolecule to the nanoscale cellulose before freeze-drying, leads to a peeling effect whereas the biomolecule intrudes into the nanoscale cellulose thus arranging more space on the nanoscale cellulose by increasing surface area where water molecules can easier bind to and/or penetrate into the cellulose structure. The higher the attraction of the biomolecule is to the amorphous NFC the more water is passed in the system.

A freeze-dried hydrogel composition is also provided, wherein the freeze-dried hydrogel composition comprises nanoscale cellulose and at least one biomolecule selected from an oligosaccharide and a disaccharide, and wherein the residual water content of the freeze-dried hydrogel composition is 0.2% (w/w)-below 2% (w/w), preferably 0.2%-1.9%, more preferably 0.3%-1.6% and most preferably 0.5%-1.3%. Typically, in the embodiments of the disclosure, the freeze-dried hydrogel composition comprises individual fibrous ribbons. Typically, the freeze-dried hydrogel composition is freeze-dried on a support, preferably in or on a bag, bottle, column, syringe or well plate, more preferably on a glass vial, 48-well plate, 96-well plate, 384-well plate or 1536-well plate, depending on the intended use. The storage is done in moisture-free sealed packages. Depending on the intended use, preserving or storing the powder of the substantially dry, freeze-dried hydrogel composition, i.e. the aerogel according to the method, process and product of the present disclosure, provides several advantages compared to storage and preservation of a wet hydrogel. The aerogel forms into hydrogel once rehydrated. In one embodiment of the disclosure there are various amounts of freeze-dried nanocellulose in the wells. When the same amount of water or cell medium is added into each well, a test panel with different cell culturing concentrations is provided.

The method and product of the present disclosure can also be used to provide freeze-dried hydrogel microparticles or freeze-dried hydrogel droplets which can be reconstituted to microbeads; to provide freeze-dried hydrogel membranes, i.e. aerogel membranes, freeze-dried for example as a sheet or in a mould, which can be wetted, i.e. reconstituted into hydrogel scaffolds or soft membranes; or to provide pre-filled microchips with freeze-dried hydrogel, which are wetted before use, alternatively forming concentration gradients enabling various cell culture conditions. One type of hydrogel scaffold of the disclosure is a stiff membrane reconstituted with a higher solid content, typically a nanofibrillar cellulose content of 3%-5%, preferably 3% to 4% (m/v). The hydrogel scaffolds may be stacked to constitute co-culture systems, for example with cells on top of between the scaffolds. Further, the freeze-dried hydrogel may be mixed with an active pharmaceutical ingredient powder (API), using nanocellulose as dispersant when wetted.

According to the embodiments of the disclosure, the mole fraction of the residual water is 5%-25%, preferably 6%-20% and more preferably 9%-15% of the freeze-dried hydrogel composition; the mole fraction of biomolecule is 50%-90%, preferably 55%-85% and more preferably 60%-80% of the freeze-dried hydrogel composition; and/or the mole fraction of nanoscale cellulose is 3-40%, preferably 10%-35% and more preferably 15%-30% of the freeze-dried hydrogel composition, preferably the nanoscale cellulose is nanofibrillar cellulose.

Moreover, a freeze-dried hydrogel composition obtainable by the method of the disclosure is provided.

Reconstitution of the of the freeze-dried hydrogel composition comprises adding a reconstitution media to the freeze-dried hydrogel composition. The reconstitution media is typically water and/or cell medium or mixtures thereof. It may also contain adding other substances or other elements, for example; cells; buffers, such as phosphate buffered saline (PBS); reinforcing materials; covering materials; active agents; and/or salts, such as NaCl. The volume of reconstitution media depends on the desired hydrogel concentration. Typically, the volume corresponds to the volume of water lost during freeze-drying, but it can be adjusted in order to for example be optimal for a specific cell type.

A preferred use of the freeze-dried hydrogel composition of the disclosure is for cell culturing. In the embodiments of the disclosure the cells are typically prokaryotic or eukaryotic cells, preferably differentiated or undifferentiated eukaryotic cells, more preferably omnipotent, pluripotent, multipotent, oligopotent or unipotent stem cells. The cells can for example be hepatocellular carcinoma cell line (HepG2), prostate cancer cell line (PC3) or human adipose/stromal cells (hASC). Typically, the cells may be prokaryotic or eukaryotic cells. For example, microbial cells may be included, such as bacterial cells or yeast cells. Eukaryotic cells may be plant cells or animal cells. Cells may be cultured cells. Examples of eukaryotic cells include transplantable cells, such as stem cells, for example omnipotent, pluripotent, multipotent, oligopotent or unipotent cells. In case of human embryonic stem cells, the cells may be from a deposited cell line or made from unfertilized eggs, i.e. "parthenote" eggs or from parthenogenetically activated ovum, so that no human embryos are destroyed. The cells can be maintained and proliferated on or in the hydrogel without animal or human based chemicals originating outside the cells. The cells may be evenly dispersed on or in the hydrogel. Thus, examples of cells include stem cells, undifferentiated cells, precursor cells, as well as fully differentiated cells and combinations thereof. In some examples the cells comprise cell types selected from the group consisting of keratocytes, keratinocytes, fibroblast cells, epithelial cells and combinations thereof. In some examples the cells are selected from the group consisting of stem cells, progenitor cells, precursor cells, connective tissue cells, epithelial cells, muscle cells, neuronal cells, endothelial cells, fibroblasts, keratinocytes, smooth muscle cells, stromal cells, mesenchymal cells, immune system cells, hematopoietic cells, dendritic cells, hair follicle cells, platelets, red blood cells, mononuclear cells, retinal pigment cells, hepatocellular carcinoma cells and combinations thereof.

Further, a cell culturing scaffold is provided, wherein the cell culturing scaffold comprises a reconstituted freeze-dried hydrogel composition of the disclosure. Typically, the cell culturing scaffold further comprises water and/or cell medium or combinations thereof, optionally together with cells.

A process for manufacturing reconstituted hydrogel, such as a cell culturing scaffold is also provided, wherein the method comprises the following steps
  a) providing a freeze-dried hydrogel composition of the disclosure;
  b) obtaining a reconstituted hydrogel by adding water, cell medium or a mixture thereof to the freeze-dried hydrogel composition to obtain a reconstituted hydrogel.

According to embodiments of the disclosure the cell medium may comprise cells or cells can be added in or on the cell culturing scaffold later. The process may further comprise adding other substances or other elements in or on top of the scaffold, for example buffers or salts, such as NaCl or adding cell medium and/or cells on top of the scaffold.

EXAMPLES

The native nanofibrillated cellulose (NFC) hydrogel used in the examples was provided by UPM, Kymmene, Finland. The concentration of the NFC was 1.5% (m/v) (GrowDex®).

Analysis Methods Used in the Examples

Rheological Measurements

Viscosity, loss—(G") and storage modulus (G') measurements were performed for the chosen NFC hydrogel compositions as triplicates with HAAKE Viscotester iQ Rheometer (Thermo Scientific, Karlsruhe, Germany). The instrument included the peltier system for temperature control and all the measurements were done at 24° C. Data from the rheological measurements were analyzed with HAAKE RheoWin 4.0 software (Thermo Fischer Scientific). The reconstituted freeze-dried NFC hydrogel compositions were rested at room temperature before the measurements.

For the shear viscosity measurements plate-on-plate geometry with parallel 35 mm diameter steel was used for all the selected compositions. The shear rate was increased from 0.1 to 1000 1/s and the results were observed with 16 timepoints. Oscillatory frequency sweep analysis was performed with double cap geometry with parallel 25 mm diameter steel. Before the measurement, constant amplitude sweeps were performed for the determination of linear viscoelastic region. Constant angular frequency ω=1 Hz with oscillatory stress between 1*10–4-500 Pa was used. Based on the linear viscoelastic region, the chosen oscillatory stress was τ=1.5 Pa for all the selected NFC hydrogel compositions and the angular frequency range was 0.6-125.7 rads-1. The results from the moduli were observed with 37 timepoints.

Freeze-Drying Protocol

Freeze-drying was performed with a laboratory-scale freeze-dryer, Lyostar II (SP Scientific Inc., USA). Different freeze-drying cycles were used based on the Tg' temperatures of the different NFC hydrogel compositions.

Evaluating Reconstitution of the Freeze-Dried Hydrogel

After freeze-drying, the elegance of the formed cakes was evaluated, and the freeze-dried NFC hydrogel compositions were reconstituted with the ultrapure water till the starting volume immediately after opening the cap of the vial. The rate of the reconstitution of the dry compositions into a hydrogel and preservation of the uniformity of the compositions were evaluated. Formed air bubbles in the reconstituted hydrogel were removed with 1 min centrifugation (1000 rpm).

Residual Water Content

Residual water contents of the freeze-dried NFC hydrogel compositions were measured with automatic colorimetric Karl Fischer titrator (Metrohm, 899 Coulometer, Switzerland). Hydranal (Coulomat AG, Fluca) was used as a solvent in the measurements. Freeze-dried NFC hydrogel compositions were diluted with 1 ml of methanol and drawn into a syringe with the volume of 0.8 ml, which were injected into a bath flask of Karl Fischer titrator. Results were given in micrograms of water and water content of methanol was considered as a blank in the calculations. Mass percentages and mole fractions of the residual water content in the freeze-dried compositions were calculated manually. All the measurements were performed as triplicates.

Scanning Electron Microscopy (SEM)

The morphology of the freeze-dried NFC hydrogel compositions was studied with a scanning electron microscope Quanta FEG250 (SEM, FEI Company, USA). The sample preparation was done manually by cutting the sample with tweezers for detection of the inner structure and surface analysis of the sample. Samples were placed on a two-sided carbon tape with silver paint. Before the imagining, samples were sputtered with platinum for 25 s with an Agar sputter instrument (Agar Scientific Ltd., UK). The homogeneity of the reconstituted freeze-dried NFC hydrogel compositions was evaluated with the light microscopy (Leica microsystems, Germany).

Example 1 Evaluating Different Hydrogel Compositions, Optimizing Rheological and Physicochemical Properties of Freeze-Dried Hydrogels Native nanofibrillated cellulose (NFC) hydrogel was provided by UPM, Kymmene, Finland with the fiber content of 1.5% (m/v) (GrowDex®). All chemicals used in this study, D-(+)-trehalose dihydrate, sucrose and glycine (99%) were purchased from Sigma Aldrich, USA.

All the studied NFC hydrogel compositions were prepared by mixing different concentrations of trehalose, sucrose or a combination of these biomolecules with ultrapure water (MQ-water), which were then combined with NFC hydrogel to the total fiber content of 0.8% (m/v). The total concentration of the biomolecules in NFC hydrogel compositions were between 50 mM-1000 mM. NFC hydrogel compositions were then homogenized by mixing them with the vortex and compositions of higher concentration than 600 mM of the biomolecules were mixed with the syringe technique based on the protocol from Paukkonen H. et al. ("Nanofibrillar cellulose hydrogels and reconstituted hydrogels as matrices for controlled drug release", International journal of pharmaceutics 532 (2017) 269-280). NFC hydrogel with the fiber content of 0.8% (m/v) without any biomolecules or organic solvents was used as a control.

Physicochemical properties of the NFC hydrogel compositions were evaluated by measuring osmotic pressure and pH. Osmotic pressure of the reconstituted freeze-dried compositions was measured with a manual freezing point osmometer (Osmomat 3000, Gonotech). Osmometer was calibrated for 0 mOsmol/kg with ultrapure water and for 100-850 mOsmol/kg with calibration standards (NaCl, Gonotech). For the measurements, samples were pipetted into measuring vessels (Gonotech) and then placed to the upper probe of the instrument. pH was measured from all the reconstituted freeze-dried NFC hydrogel compositions with pH paper (Macherey-Nagel, Germany). The measurements were repeated after the freeze-drying and reconstitution.

To optimize freeze-drying temperatures, the glass transition temperatures (Tg') of all the NFC hydrogel compositions and the controls were measured with differential scanning calorimetry (DSC) (TA instruments). NFC hydrogel compositions were pipetted to a hermetically sealed T-Zero pans (40 µl). Measurements were carried out by first decreasing the temperature from +40° C. to −80° C. and then heating 10° C./min to +20° C. with a cell purge gas flow (N2) 50 ml/min. Temperature and heat flow were calibrated with indium.

Glass transition temperature measurements were done as triplicates and results were analyzed with TRIOS software (TA Instruments). Two NFC hydrogel compositions, comprising 150 mM of trehalose, 333 mM of glycine and 700 mM of DMSO or glycerol, with Tg' lower than −50° C. were eliminated.

Freeze-drying was performed with a laboratory-scale freeze-dryer, Lyostar II (SP Scientific Inc., USA). Two different freeze-drying cycles were used based on the Tg' temperatures of the different NFC hydrogel compositions. Freezing step was performed at −55° C./at −47° C. (1° C./min) for 2 hours, after which temperature was increased 1° C./min till −50° C./till −42° C. and the pressure was decreased to 100 mTorr/to 50 mTorr. Primary drying was determined with a comparative pressure measurement using a capacitance manometer (absolute pressure, CM) and pirani gauche (relative vacuum). Freeze-drying was then continued to the secondary drying where temperature was gradually increased 1° C./min from −50° C./from −47° C. to +20° C. Total length of the first freeze-drying cycle was 54 hours and for the second 143 hours. The sample volume was 0.2 ml or 1.75 mi depending on the intended experiment. NFC hydrogel compositions were freeze-dried in Schott Toplyo® injection vials (Adelphi) with the volume of 2 ml or 6 ml depending on the sample size. Vials were closed with rubber Daikyo D Sigma freeze-drying stoppers (Adelphi). After the freeze-drying All-Aluminium Crimp seals (West Pharmaceutical Services) were placed on the vials. The freeze-dried samples were stored at +4° C. before further experiments.

The cakes of the freeze-dried NFC hydrogel compositions including 150 mM of trehalose and 666 mM of glycine were collapsed and the ones including 750 mM-1000 mM of trehalose showed shrinkage. Slight cracking of the formed cakes was observed for the freeze-dried control and the freeze-dried NFC hydrogel compositions including 50 mM-250 mM sucrose or trehalose. Elegant, white and solid cakes were obtained with the freeze-dried NFC hydrogel compositions including 300 mM of sucrose and/or trehalose and with the one including 150 mM of trehalose and 333 mM of glycine.

The freeze-dried (FD) NFC hydrogel compositions were reconstituted with the ultrapure water (MQ-water) till the starting volume immediately after opening the cap of the vial. The rate of the reconstitution of the dry compositions into a hydrogel and preservation of the uniformity of the NFC composition were evaluated.

Dissolving of the collapsed and shrunken cakes failed when the ultrapure water of the original volume was added, which is why they were eliminated. In addition, the freeze-dried control formed aggregates after reconstitution, which were impossible to homogenize.

After the reconstitution of the freeze-dried NFC hydrogel compositions with the successful cake appearance, the colour of the cakes changed immediately to transparent and hydrogel was formed after 2 minutes of a gentle, manual stirring. To remove formed air bubbles inside of the reconstituted freeze-dried NFC hydrogel compositions, the samples were centrifuged 1 min centrifugation (1000 rpm), after which they corresponded to the NFC hydrogel compositions before the freeze-drying.

Physicochemical properties were evaluated by measuring osmotic pressure and pH of the reconstituted freeze-dried NFC hydrogel compositions including different concentrations of trehalose, sucrose and glycine. Osmotic pressure increased with the increasing biomolecule concentration and compositions with the concentration between 50 mM-300 mM of trehalose or sucrose had the corresponding osmotic pressures between 50 mOsmol/kg-300 mOsmol/kg. A slight decrease could be observed in the osmotic pressures after the freeze-drying and reconstitution of all the NFC hydrogel compositions.

Light microscopy images showed similar homogeneity between the reconstituted freeze-dried NFC compositions including biomolecules and the NFC compositions including biomolecules before the freeze-drying. The homogeneity could not be observed from the reconstituted freeze-dried control, since the light microscopy images after the freeze-drying process showed unorganized, crystallized features.

Reconstituted freeze-dried NFC hydrogel composition including 300 mM of both trehalose and sucrose had osmotic pressure higher than the calibration range 0-850 mOsmol/kg and was eliminated from the subsequent experiments. pH of all the compositions were between 6-7 and remained the same after freeze-drying and reconstitution.

After the optimization of the freeze-drying process, preserved properties of the freeze-dried NFC composition hydrogels and of the reconstituted ones had to be ensured.

Based on the organized porous structure of the cake after freeze-drying, the viscosity measurements were performed for three different reconstituted freeze-dried NFC hydrogel compositions, comprising 300 mM of sucrose or trehalose and the one comprising 150 mM of trehalose and 333 mM of glycine. The oscillatory frequency sweep analysis was performed for the last two compositions including only 300 mM of sucrose or trehalose based on the viscosity measurements and more suitable Tg' temperatures, which were over −40° C.

Figure 1B:
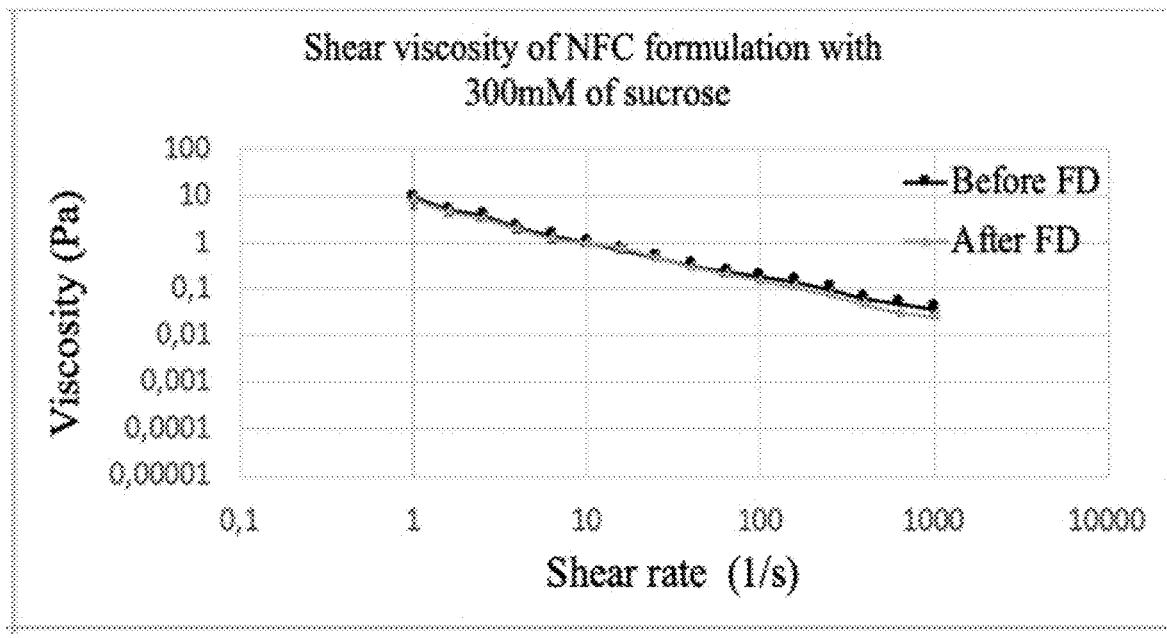
FIG. 1B shows shear rate viscosity before freeze-drying (FD) and after the reconstitution of the freeze-dried cake from nanofibrillar cellulose (NFC) hydrogel composition with 300 mM of sucrose (mean±S.D., n=3)
Figure 1C:
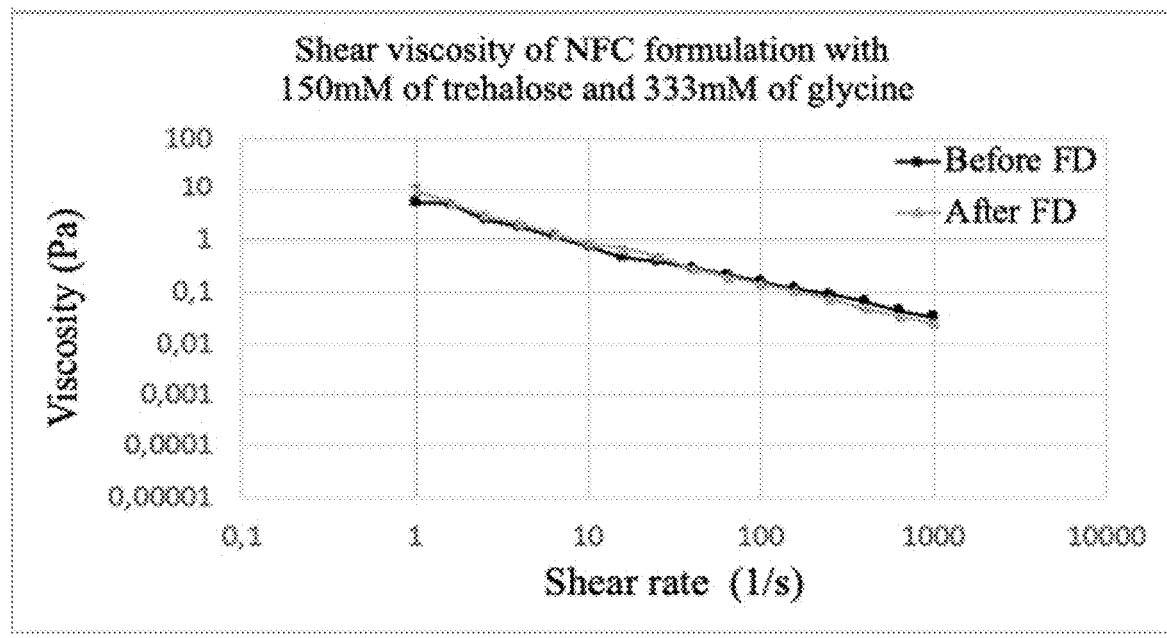
FIG. 1C shows shear rate viscosity before freeze-drying (FD) and after the reconstitution of the freeze-dried cake from nanofibrillar cellulose (NFC) hydrogel composition with 150 mM of trehalose (mean±S.D., n=3)
Figure 1D:
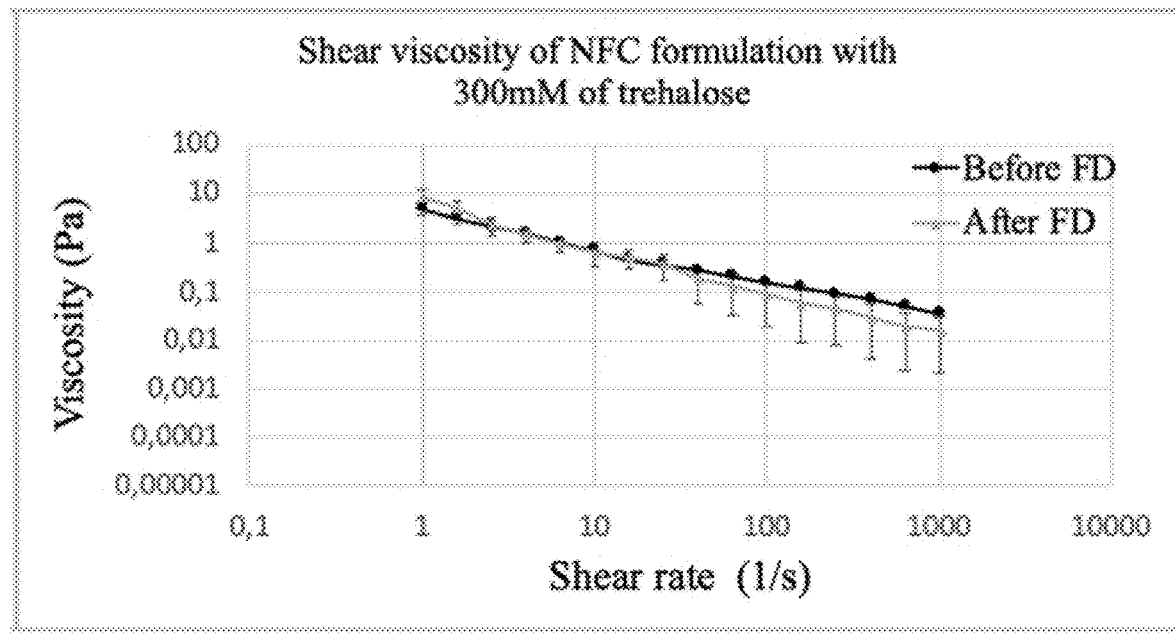
FIG. 1D shows shear rate viscosity before freeze-drying (FD) and after the reconstitution of the freeze-dried cake from nanofibrillar cellulose (NFC) hydrogel composition with 300 mM of trehalose (mean±S.D., n=3)

Addition of the biomolecules did not affect significantly on the viscosity properties of NFC hydrogel compositions before the freeze-drying, which was linearly decreasing when the shear rate was increased. Unlike in the case of the reconstituted freeze-dried control in FIG. 1A, the shear viscosity was preserved with the presence of the biomolecules in the reconstituted freeze-dried NFC hydrogel formulations as observed from the FIGS. 1B-D. Compositions including sucrose of FIG. 1A) or a combination of glycine and trehalose of FIG. 1B showed equal viscosity properties before and after freeze-drying.

Figure 2A:
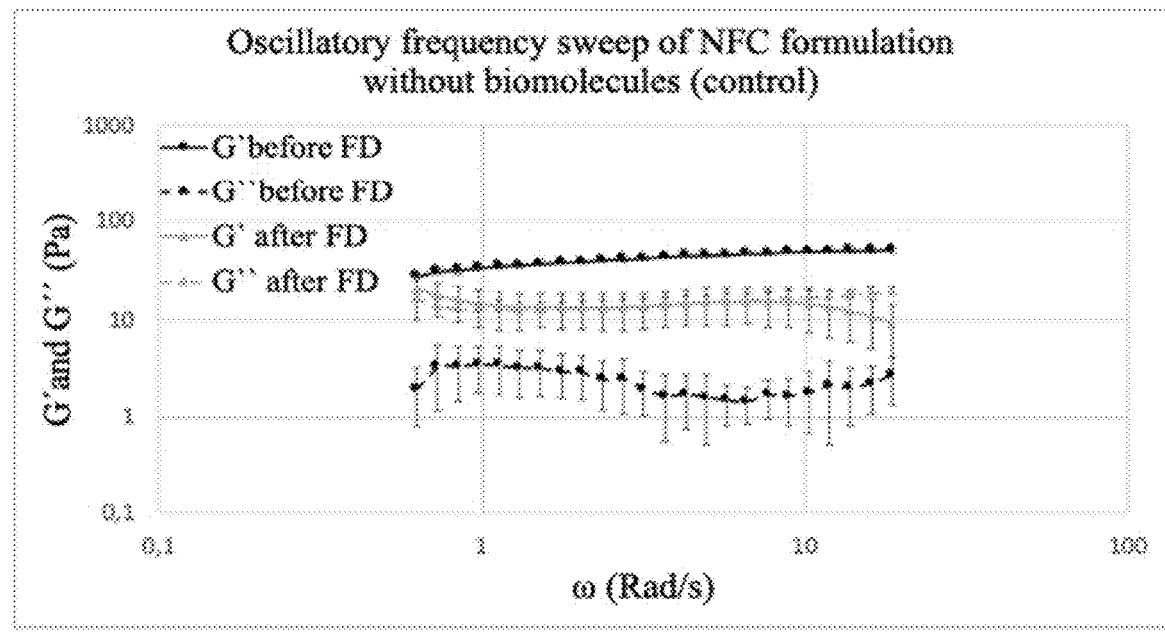
FIG. 2A shows storage modulus (G') and loss modulus (G") before freeze-drying and after the reconstitution from nanofibrillar cellulose (NFC) composition without biomolecules (mean±S.D., n=3)
Figure 2B:
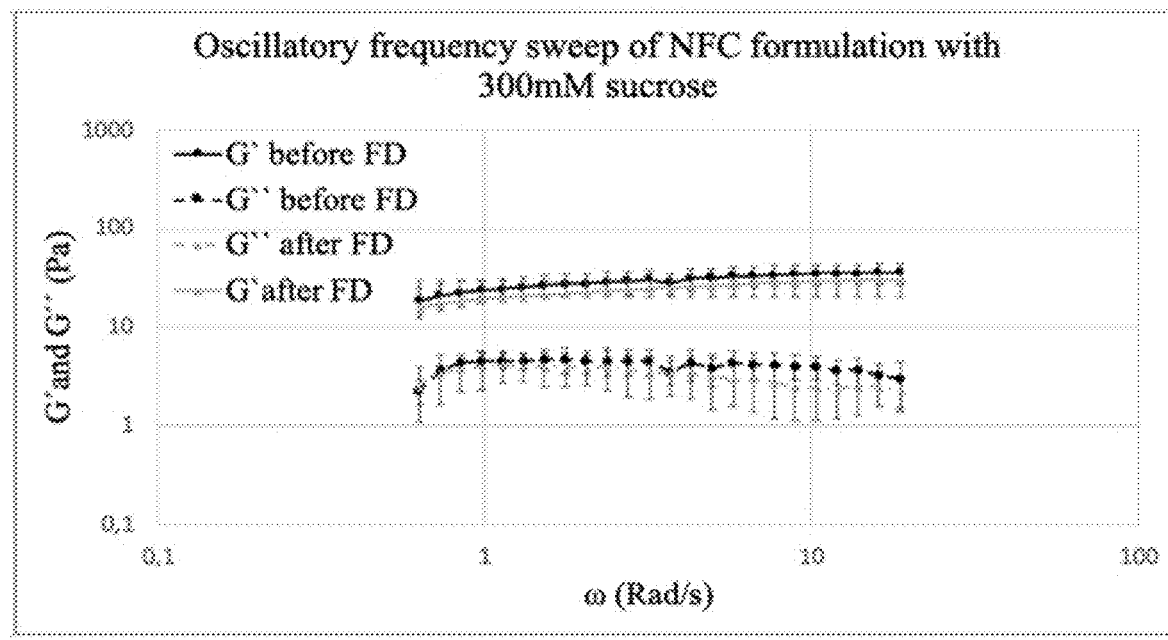
FIG. 2B shows storage modulus (G') and loss modulus (G') before freeze-drying and after the reconstitution from nanofibrillar cellulose (NFC) composition with 300 mM of sucrose (mean±S.D., n=3)
Figure 2C:
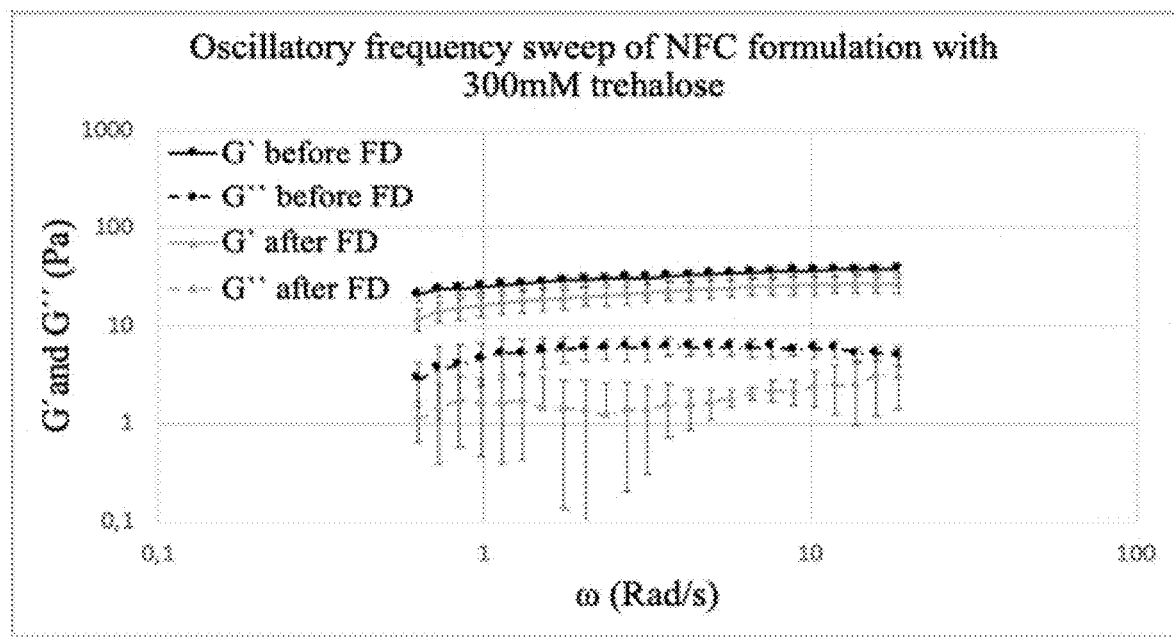
FIG. 2C shows storage modulus (G') and loss modulus (G") before freeze-drying and after the reconstitution from nanofibrillar cellulose (NFC) composition with 300 mM of trehalose (mean±S.D., n=3)

Viscoelastic properties were studied of the final two reconstituted freeze-dried NFC hydrogel compositions including 300 mM of sucrose or trehalose and from the control one. Before the freeze-drying G' were equal between the NFC hydrogel compositions with and without the biomolecules and they were above G'' as shown in FIG. 2A-C. After the freeze-drying and reconstitution, the moduli of the control crossed each other and differed significantly from the ones before the freeze-drying as shown in FIG. 2A. Reconstituted freeze-dried NFC hydrogel composition containing 300 mM of sucrose had equal G' moduli with the one before the freeze-drying as shown in FIG. 2B. G' of the reconstituted freeze-dried NFC hydrogel composition with 300 mM of trehalose were slightly decreased compared with the same composition before the freeze-drying process as shown in FIG. 2C.

To ensure that the remained compositions were correctly freeze-dried, mass percent of the residual water content in the freeze-dried NFC hydrogel compositions were measured. All the compositions contained less than 3% (w/w) of residual water except for the control.

To illustrate in more detail the proportion of water of the freeze-dried the mole fraction of the residual water content was calculated. The results are shown in Table 1. The molecular weight of NFC was considered to be the molecular weight of the glucose monomer in the calculations and the mole fraction of water was theoretically calculated to be over 99% in all the NFC hydrogel compositions before the freeze-drying. After the freeze-drying the mole fraction of the residual water content in the freeze-dried control was measured to be around 35%. All the freeze-dried NFC hydrogel compositions showed mole fraction of the residual water content to be under 30%.

TABLE 1

| Concentration of the biomolecules (mM) | Residual water content (w-%) | Mole fraction of residual water (%) | Mole fraction of biomolecules (%) | Mole fraction of NFC (%) |
| --- | --- | --- | --- | --- |
| 100T | 0.77 | 9.8 | 58.4 | 31.8 |
| 200T | 0.59 | 8.6 | 72.6 | 18.8 |
| 300T | 0.73 | 11.8 | 75.2 | 13.0 |
| 500T | 0.66 | 10.1 | 81.5 | 8.4 |
| 700T | 1.12 | 11.6 | 82.3 | 6.1 |
| 1000T | 1.15 | 10.5 | 85.1 | 4.4 |
| 100S | 0.37 | 5.0 | 63.6 | 31.4 |
| 200S | 0.49 | 6.9 | 74.7 | 18.4 |
| 300S | 1.00 | 14.9 | 73.1 | 12.0 |
| 500S | 1.08 | 14.3 | 78.0 | 7.7 |
| 700S | 1.14 | 14.6 | 79.8 | 5.6 |
| 1000S | 1.56 | 18.6 | 77.6 | 3.8 |

T = trehalose, S = sucrose

As can be seen from the results, the amount of biomolecule impacts on the residual water content and mole fraction of residual water. Thus, it is possible to optimize the residual water content by adding different biomolecules and amounts of biomolecules to the hydrogel before freeze-drying it, in order to get a freeze-dried hydrogel which can be reconstituted.

Based on these results, freeze-drying of hydrogel comprising NFC hydrogel was especially successful with an NFC hydrogel composition comprising 300 mM of sucrose as biomolecule. Having sucrose as the only lyoprotective compound with NFC hydrogel have many benefits compared to other studied biomolecules. For example, compared to NFC hydrogel compositions including glycine, the primary drying temperature could be increased from −50° C. to −42° C. Moreover, the porous, organized morphology and the physicochemical properties, such as iso-osmotic solution, pH neutral environment and non-toxicity of the NFC hydrogel composition with sucrose are beneficial for different uses.

Example 2 Preparing NFC Compositions for Cell Culturing

Freeze-dried hydrogel was prepared using 300 mM sucrose and 1.5% nanofibrillar cellulose (NFC). The sucrose was mixed into the NFC hydrogel and the samples were freeze-dried (LyoStar II, SP Scientific) on a low adhesion 96-well plate.

The nanofibrillar cellulose was native NFC hydrogel provided by UPM, Kymmene, Finland with a fiber content of 1.5% (m/v) (GrowDex®) and the sucrose was purchased from Sigma Aldrich, USA.

The freeze-drying cycle was as follows. Freezing was performed by lowering the temperature 1° C./min until a temperature of −47° C. was reached. The Freezing was continued at ATM for 3 hours. The primary drying was performed at a temperature of −42° C. and a pressure of 50 mTorr (6.67 Pa) for 94 hours. During the secondary drying the temperature was gradually increased was performed by rising the temperature 1° C./min from −42° C. to 20° C. The pressure was 50 mTorr (6.67 Pa) and the secondary drying was continued for 1.5 hours.

The freeze-dried hydrogel was packed and sealed from air moisture and stored at room temperature for months.

Example 3 Culturing 3D Cell Spheroids in Freeze-Dried and Reconstituted NFC Hydrogels Suitability of the freeze-dried and reconstituted NFC hydrogels of Example 2 for 3D cell culturing were studied. The studied cells were hepatocellular carcinoma cell line (HepG2), prostate cancer cell line (PC3) and human adipose/stromal cells (hASC).

The freeze-dried 1.5% NFC hydrogel samples were reconstituted directly to different NFC concentrations. The samples were reconstituted with mixtures of MO-water, NaCl, cell media and/or cells. Ph was controlled to be in physiological range. The cell medium was bicarbonate buffered nutrient mixture with fetal bovine serum. For the reconstituted freeze-dried hydrogel reconstituted with only MO-water, the volume used was the volume of water lost in freeze-drying. For the mixtures of MQ-water and cell medium, the amount of MQ-water was the volume of water lost in freeze-drying and for cell medium, the amount needed for dilution.

The NFC hydrogel concentrations of the reconstituted hydrogels comprising MQ-water, cell medium and cells were adjusted to optimal hydrogel stiffness for selected cell types. The used concentrations were 0.8%, 1.0% and 0.125% for HepG2, PC3 and hASC cells, respectively. Storage modulus (G') and loss modulus (G") of reconstituted compositions were measured with Viscotester (Thermo Scientific) and compared to those of the fresh hydrogels. Osmolarity was measured with Osmomat 3000 (Gonotec) and optimized to be suitable for cell culturing (280-320 mOsmol/kg) by changing the composition of reconstitution media. It was concluded that osmolarity, pH, storage modulus and loss modulus of reconstituted NFC hydrogel compositions remained unchanged after freeze-drying and reconstitution. Reconstitution of native NFC into different native NFC concentrations after freeze-drying was possible independent of the starting native NFC concentration.

Figure 3A:
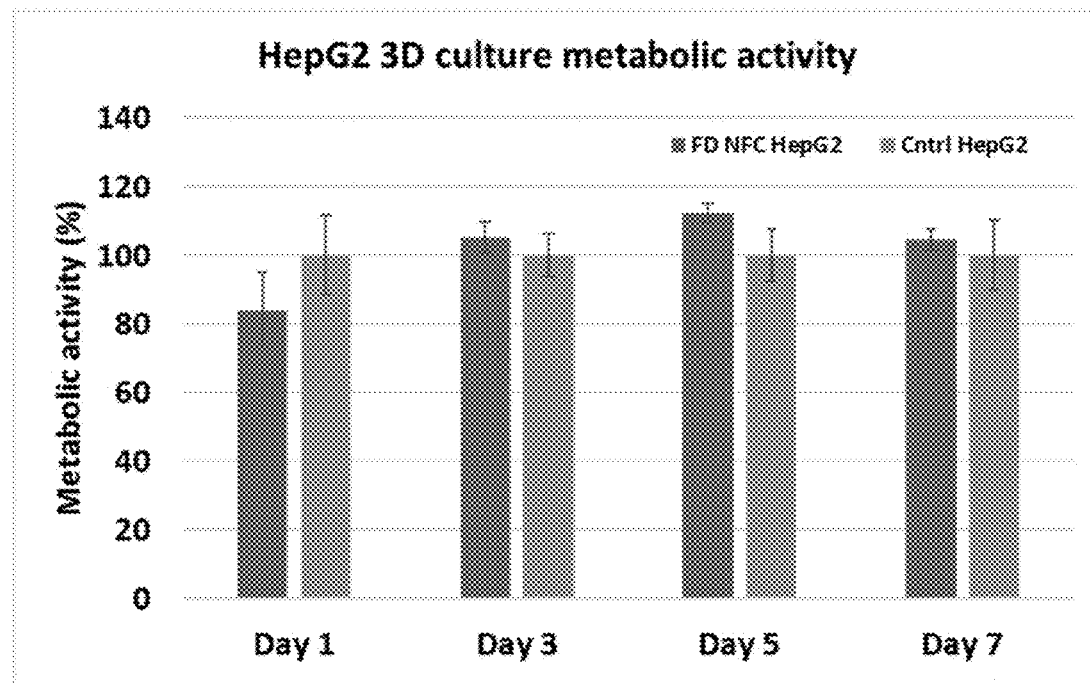
FIG. 3A shows 3D viability of HepG2 cell spheroids cultured in reconstituted freeze-dried (FD) hydrogels and fresh, non-freeze-dried hydrogel (Cntrl)
Figure 3B:
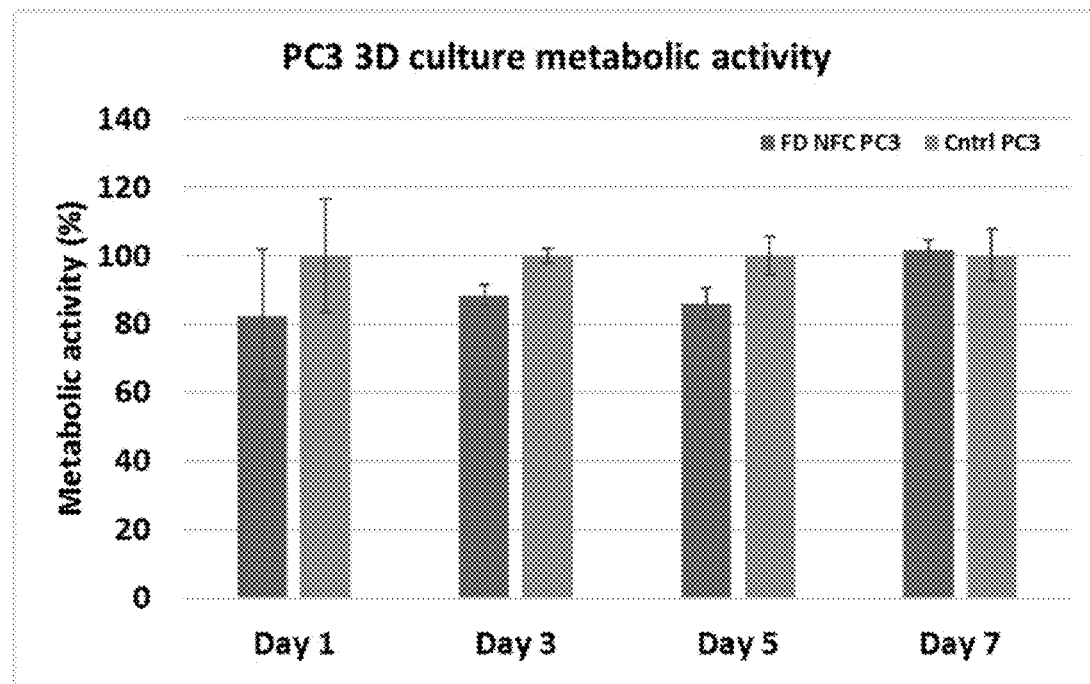
FIG. 3B shows 3D viability of PC3 cell spheroids cultured in reconstituted freeze-dried (FD) hydrogels and fresh, non-freeze-dried hydrogel (Cntrl)

The reconstituted NFC hydrogel, media and cells were mixed by pipetting and reservoir media was added on the top of the hydrogel-cell-suspension. 3D cell spheroids were cultured at 37° C. with $CO_2$ with earlier established protocols (such as described in Bhattacharya et al., "Nanofibrillar cellulose hydrogel promotes three-dimensional liver cell culture", Journal of controlled release: official journal of the Controlled Release Society. 164 (2012) 291-8) and the same protocols were used for both the reconstituted hydrogels as well as for non-freeze-dried hydrogels used as controls. Viability of the cell spheroids was studied for 7 days, i.e. on day 1, 3, 5 and 7 with an alamarBlue cell viability assay. The size of the cell spheroids was evaluated with microscope over the 7 days study period. The results of the viability tests are shown in FIG. 3A for HepG2 cell spheroids and in FIG. 3B for PC3 cell spheroids. The left columns show the results for the freeze-dried NFC and the right columns the control.

The tests showed that the freeze-dried hydrogel could be reconstituted in different concentrations and that reconstituted freeze-dried hydrogels were as suitable for cell culturing as fresh, non-freeze-dried hydrogel. Both HepG2 and PC3 cells were successfully cultured for 7 days in freeze-dried and reconstituted native NFC hydrogel.

Example 4 Molecular Dynamics Simulations

The interactions between water, excipients and NFC were studied with molecular dynamics (MD) simulations. The MD simulations were run to study the dynamic behaviour of the system and to gain specific mechanistic insights.

Three plane-like simulation systems were developed: cellulose in a crystalline morphology to determine the binding free energies, one with a hydrophobic surface and one with a hydrophilic surface, and cellulose in an amorphous morphology to determine the biomolecules' effects on water penetration.

To the equilibrated water systems excipients were added at random positions of the water phase in concentrations according to the number of water molecules. Thus, three new systems were generated from each system with the following concentrations of biomolecules: 300 mM of trehalose, 150 mM of trehalose with 333 mM of glycine, and 300 mM of saccharose. Additional simulation systems were generated for different monosaccharides and disaccharides with the following concentrations of biomolecules: 300 mM of fructose, glucose, lactose, sucrose (saccharose), trehalose and xylitol, 225 mM of each saccharide combined with 75 mM of glycine and 200 mM of each saccharide combined with 100 mM of glycine.

Three properties were of particular interest: the free energy difference between the excipients and the cellulose layer, water penetration in amorphous systems and the chain peeling effect of the sugars in crystalline systems noticed during visualization. The free energy differences were determined by producing the potentials of mean force from the partial densities of the excipients via gmx density. The more stable side of the cellulose plane was used to quantify the free energy difference. Water penetration was calculated with the average number of water molecules within 1 nm of a plane along the x- and y-axes formed by the centre of mass of cellulose using gmx select. The average number of glucoses within the same area was determined with the same method, with the exception of using carbon molecules and dividing it by 6. Lastly, gmx rms was used on the eight chains on the top and bottom of both crystalline cellulose layers to determine the RMSD of those individual chains, which gave a metric on the chain peeling as a function of time.

Figure 4:
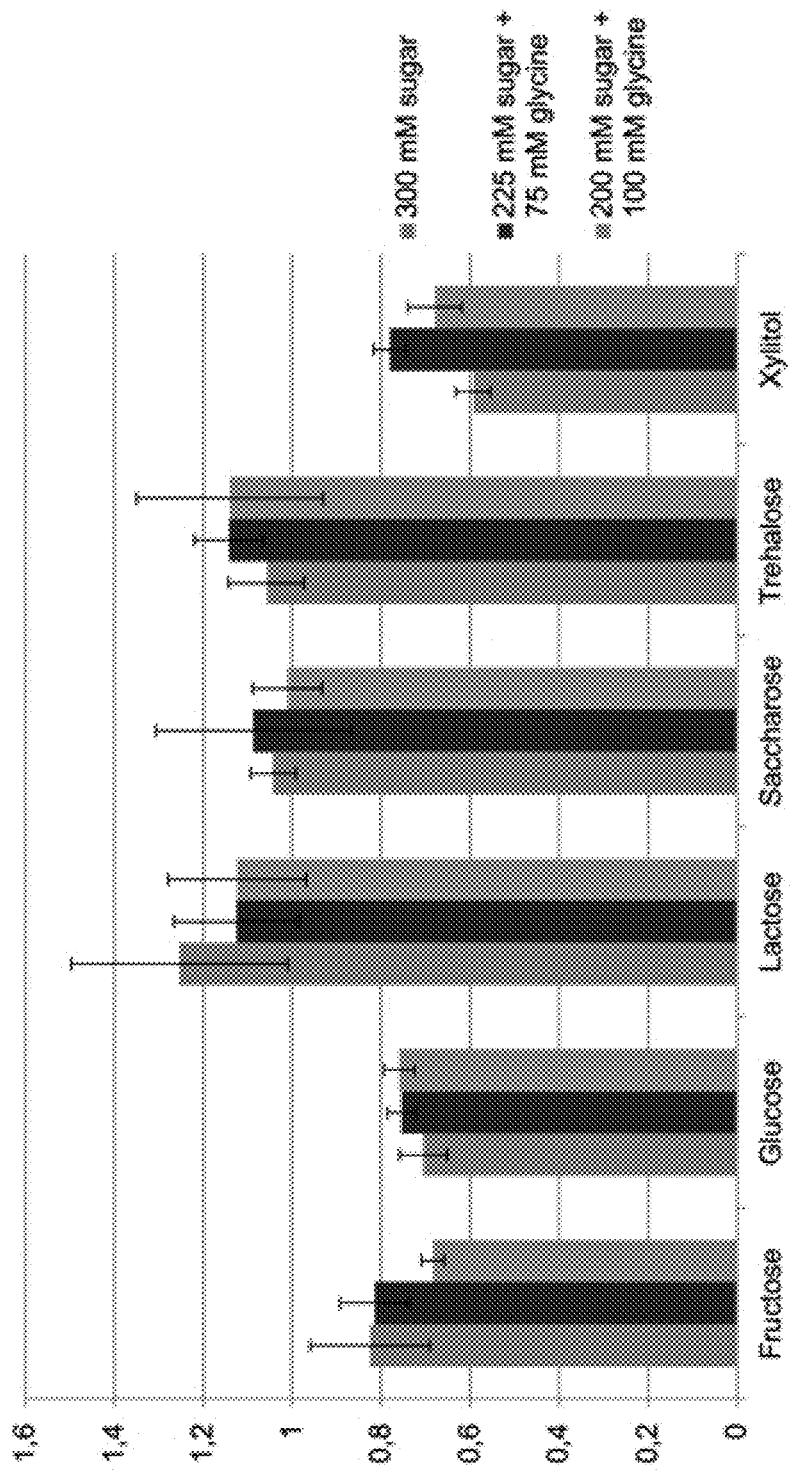
FIG. 4 shows the binding free-energies for different monosaccharides and disaccharides studied with and without glycine molecules.

The results for the binding of excipients to the surface of NFC were consistent between different cellulose planes. The results of the additional simulations with different monosaccharides and disaccharides indicate that all saccharide molecules have a preference to concentrate on the NFC-water interface. The binding strength, however, differs between the systems. The highest binding free energies were registered for saccharose and lactose as can be seen in FIG. 4. Lower surface interactions were seen in the case of fructose, glucose, and xylitol. The left column for every saccharide shows the results for 300 mM of saccharide, the column in the middle shows the results of 225 mM of each saccharide combined with 75 mM of glycine and the right column shows the results for 200 mM of each saccharide combined with 100 mM of glycine.

Glycine was shown to have no attraction to the surface of NFC. In the 300 mM concentration systems, sucrose proved to have a higher attraction to the cellulose plane than trehalose. With a hydrophobic cellulose plane, the difference between the free energies was 0.54 kJ/mol. Similarly, systems with half the concentration of trehalose and 333 mM of glycine had a slight but significant increase in trehalose attraction, with a 0.56 kJ/mol difference between free energies. The respective differences with a hydrophilic plane were 0.38 kJ/mol and 0.20 kJ/mol. Additional tests comparing 300 mM sucrose and 200 nM sucrose together with 100 mM of one of glycine, leucine, tryptophan or glutamine showed that generally amino acids improve the attraction of sucrose to cellulose. Both tryptophan and glutamine penetrated the cellulose plane, but glutamine showed no attraction. Tryptophan showed a significantly higher attraction than saccharose. Also sugar-cellulose hydrogen bonds seems to increase with the addition of amino acids (except for glycine).

Figure 5:
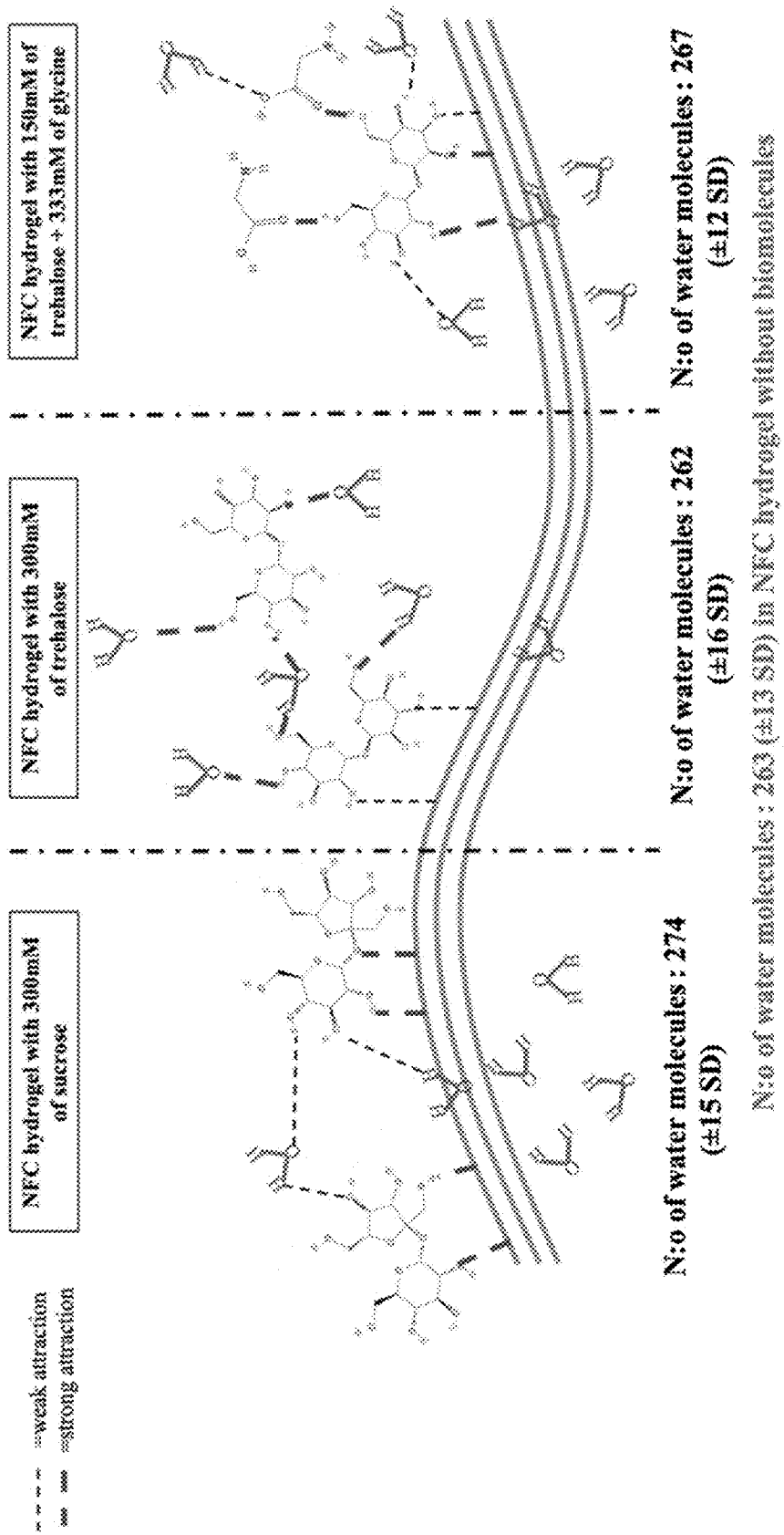
FIG. 5 shows water molecules penetration of the amorphous cellulose plane of nanofibrillar cellulose with 300 mM of sucrose, with 300 mM of trehalose and with 150 mM of trehalose and 333 mM of glycine.

The biomolecules had different effects on the residual water content. Water molecules penetrated the amorphous cellulose plane readily, unlike the sugars despite their attraction as shown in FIG. 5. Without excipients, on average 263 (±13 SD) water molecules resided inside a 2 nm slice of amorphous cellulose. With the added saccharose, water penetration increased to 274 (±15 SD). Added trehalose, however, didn't have an effect (262±16 SD). A reduced amount of trehalose with glycine raised water penetration slightly to 267 (±12 SD). By determining the average number of glucose molecules within the same area, the following ratios of water:glucose were received: 1.385 for pure water, 1.424 for 300 mM saccharose, 1.378 for 300 mM trehalose and 1.400 for 150 mM trehalose with 333 mM glycine. This might be explained by the different attractions of the biomolecules to the nanocellulose system; the higher the attraction of the biomolecule was to the amorphous NFC the more water was passed in the system. The reason for this might be that the tighter attraction gives more space for water molecules to access inside the amorphous NFC. The ability of water to penetrate more into amorphous NFC comprising sucrose than for example trehalose could be an advantage in reconstitution of the freeze-dried NFC hydrogel composition.

During visualization, a chain peeling effect was discovered in the crystalline systems. As the cellulose chains are not connected between periodic images, the chain ends at the joints can move freely into water. This effect was not significant in pure water systems. However, the added sugars, especially trehalose, were able to peel away these chain ends further into the water phase. Additionally, after pulling a chain away from the crystalline structure, the sugars were able to move into the formed cleft, preventing the chain from returning. In order to quantify this effect, the root mean square deviations (RMSD) of the surface chains were determined as a function of time. As a chain end is pulled from the structured crystalline structure into the chaotic water phase, its RMSD increases. In hydrophobic systems, the cut off for a chain being pulled away from the crystalline structure was at −0.15 nm and for hydrophilic systems at −0.35 nm. The surface chains of the hydrophilic plane are more prone to movement due to their hydrophilicity. The results indicate that trehalose and sucrose molecules can promote the chain peeling at the NFC surface compared to the system without excipients.

Figure 6:
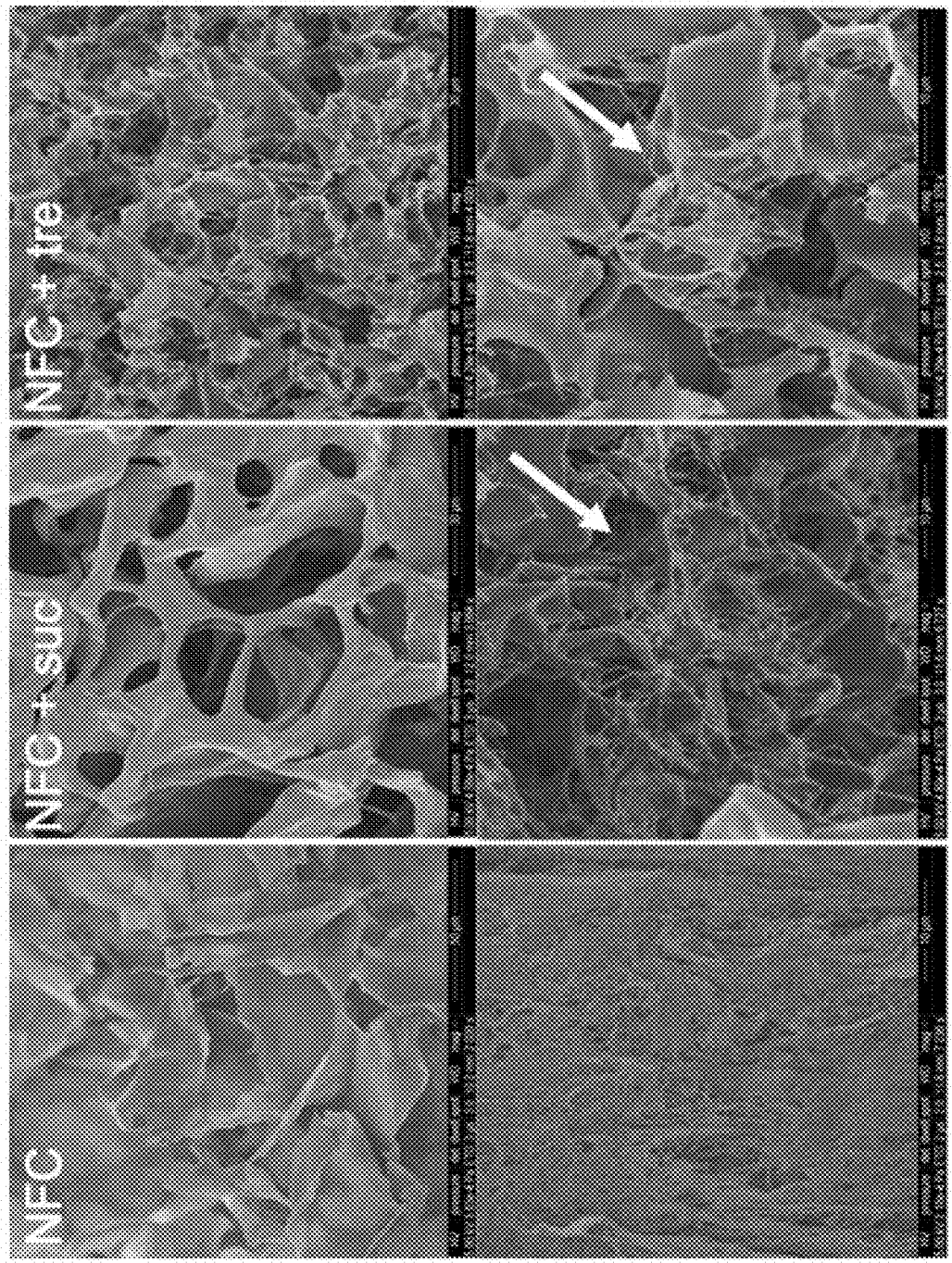
FIG. 6 shows SEM images of freeze-dried nanofibrillar cellulose (NFC) formulation without the excipients (NFC), with 300 mM of sucrose (NFC+SUC), 300 mM of trehalose (NFC+TRE) as well as zoomed images of the same compositions.

When the magnification was increased, fibrous structure stood out from the SEM images of the freeze-dried control with the width around 15 nm. Individual fibrous ribbons could also be observed from the freeze-dried compositions with sucrose or trehalose. FIG. 6 shows SEM images of freeze-dried NFC composition without the excipients, with 300 mM of sucrose and 300 mM of trehalose as well as zoomed images of the same compositions. Arrows indicate an example of the individual fibrous ribbon observed in the compositions. This might be caused by the ability of these biomolecules to peel chains as evidenced in the simulations of crystalline NFC.

In light of the present simulation results, it is clear that trehalose and sucrose molecules can interact with the NFC surface and change NFC's structure by facilitating the peeling of surface chains, which partially explains the experimentally registered differences in the morphology of NFC after FD. Although glycine has no attraction to the NFC's surface, simulations highlighted the effect of glycine on the binding trehalose on the NFC surface. Namely, in the hybrid system of glycine and trehalose, the binding of trehalose to the surface of NFC was slightly more robust, reaching the same binding free-energy value when compared to sucrose without glycine. Besides, the simulation results suggest that the chain peeling of NFC was not taking place in crystalline and hydrophobic NFC surface with glycine, which might lead to more preserved stability and structure of NFC matrixes in aqueous surroundings before and after freeze-drying.

The invention claimed is:

1. A method for controlling freeze-drying of a hydrogel comprising nanoscale cellulose, wherein the method comprises:
   a) providing a hydrogel comprising nanoscale cellulose;
   b) providing at least one biomolecule selected from an oligosaccharide or a disaccharide, the amount of the at least one biomolecule being 250 mM to 500 mM;
   c) mixing the hydrogel of step a) with the at least one biomolecule of step b) to obtain a mixture; and
   d) freeze-drying the mixture of step c) to obtain a freeze-dried hydrogel comprising nanoscale cellulose, wherein the residual water content of the freeze-dried hydrogel is 0.2% (w/w)-below 2% (w/w); and
   wherein the freeze-dried hydrogel is reconstitutable to the original hydrogel concentration or to a different hydrogel concentration.

2. The method according to claim 1, wherein the freeze-drying comprises a freezing step, a primary drying step, and a secondary drying step, the residual water content being water remaining in the freeze-dried hydrogel that is not released during the secondary drying step.

3. The method according to claim 1, wherein the nanoscale cellulose is chosen from nanofibrillar cellulose and/or nanocrystals.

4. The method according to claim 1, wherein the at least one biomolecule is a disaccharide.

5. The method of claim 1, further comprising:
   e) reconstituting the freeze-dried hydrogel to the original hydrogel concentration or to a different hydrogel concentration.

6. The method of claim 1, wherein the composition is configured to be used for culturing eukaryotic cells.

* * * * *